(12) United States Patent
Olofsson (10) Patent No.: US 6,664,776 B2
(45) Date of Patent: Dec. 16, 2003

(54) METHOD AND SYSTEM FOR VOLTAMMETRIC CHARACTERIZATION OF A LIQUID SAMPLE

(75) Inventor: Arnold Olofsson, Täby (SE)

(73) Assignee: OTRE AB, Stockholm (SE)

( * ) Notice: Subject to any disclaimer, the term of this patent is extended or adjusted under 35 U.S.C. 154(b) by 0 days.

(21) Appl. No.: 10/025,565

(22) Filed: Dec. 18, 2001

(65) Prior Publication Data

US 2003/0111993 A1 Jun. 19, 2003

(51) Int. Cl.[7] .................. G01N 27/00; G01N 27/02; G01R 27/08
(52) U.S. Cl. .................. 324/71.1; 324/444; 324/693; 324/722
(58) Field of Search ................. 324/71.1, 439, 324/444, 676, 693, 691, 710, 713, 714, 715, 722, 723; 204/402, 403.03, 406, 411, 412, 400, 434; 205/782.5, 783, 786, 787

(56) References Cited

U.S. PATENT DOCUMENTS

| | | | | |
|---|---|---|---|---|
| 4,614,577 A | * | 9/1986 | Mund et al. | 204/403.06 |
| 4,897,162 A | * | 1/1990 | Lewandowski et al. | 205/786 |
| 5,326,447 A | * | 7/1994 | Fletcher | 205/782.5 |
| 5,873,990 A | * | 2/1999 | Wojciechowski et al. | 204/406 |
| 5,980,708 A | * | 11/1999 | Champagne et al. | 204/406 |
| 6,280,633 B1 | * | 8/2001 | Conrad et al. | 210/739 |

FOREIGN PATENT DOCUMENTS

| | | | |
|---|---|---|---|
| WO | WO 99/13325 | 3/1999 | G01N/27/416 |
| WO | WO 99/46201 | 9/1999 | |
| WO | WO 00/67011 | 11/2000 | |
| WO | WO 01/89189 A2 | 11/2001 | |

OTHER PUBLICATIONS

D. Sauter et al., *Development of Modular Ozone Sensor System for Application in Practical Use*; Sensors and Actuators B. Elsevier Sequoia, S.A., Lausanne, Ch.; Sep. 10, 2000; pp. 1–9; XP004208551.

T. Ohmi, et al., *Ozone Decomposition in Ultrapure Water and Continuous Ozone Sterilization for a Semiconductor Ultrapure Water System*; Journal of Electrochemical Society, U.S. Electrochemical Society; Manchester, New Hampshire; vol. 139, No. 11; Nov. 1, 1992; pp. 3336–3345; XP000360633.

P. Ivarsson et al., *Discrimination of Tea by Means of a Voltammetric Electronic Tongue and Different Applied Waveforms*; Sensors and Actuators B 76 (2001); pp. 449–455; PD; Jun. 1, 2001.

Holmin et al., *Compression of Electronic Tongue Data Based on Voltammetry–A Comparative Study*; Sensors and Actuators B 76 (2001); pp. 455–464; PD; Jun. 1, 2001.

Winquist, Fredrik et al., "Monitoring of Freshness of Milk by an Electronic Tongue on the Basis of Voltammetry". XP–000861720 (1998). pp. 1937–1946.

Winquist, Fredrik et al. "An Electronic Tongue Based on Volammetry". Analytica Chimica Acta (1997). vol. 357. pp. 21–31.

* cited by examiner

*Primary Examiner*—N. Le
*Assistant Examiner*—John Teresinski
(74) *Attorney, Agent, or Firm*—Jenkens & Gilchrist, PC (57) ABSTRACT

Parallel measurements on a plurality of working electrodes E1–E4 during the same pulse-sequence permits voltammetric characterization by, during each cycle of a predetermined pulse-sequence, performing a predetermined number of measurement procedures, each including the steps of: 1) removing the applied first potential P1 from all but one of the working electrodes E1–E4, 2) registering the current passing through the working electrode E1, E2, E3 or E4 still having the first potential P1 applied thereto, 3) storing the registered value in a data storage unit, and 4) applying the first potential P1 on all working electrodes. Thereafter, the stored values are analyzed using a predetermined mathematical model to produce a result.

10 Claims, 5 Drawing Sheets

METHOD AND SYSTEM FOR VOLTAMMETRIC CHARACTERIZATION OF A LIQUID SAMPLE

The present invention relates to a method and a system for detecting different characteristics indicative of a desired property of a sample, and in particular to a method and a system for voltammetric characterization of a liquid sample.

BACKGROUND OF THE INVENTION

In WO 99/13325 there is disclosed a method for detecting different characteristics indicative of a desired property of a sample, such as the concentration of an analyte, pH etc. Said method is based on voltage pulses according to a pulse-sequence comprising a plurality of pulses in sequence and at different amplitudes, being applied to electrodes. The obtained response signals are used as input to a pattern recognition program in a computer for interpretation and for outputting results. The analysis is based on multivariate methods, such as PCA (Principal Component Analysis). A brief account of PCA is given in an article by F. Winquist et al in "An electronic tongue based on voltammetry", Analytica Chimica Acta, 357 (1997) 21–31. This article and the WO publication are both incorporated herein in their entirety by reference.

The above method is essentially characterized by.

Use of pulse voltammetry (or other electrical measurement methods) to obtain information (transient curves);

Use of different electrode materials, modified electrodes or pulse-sequences etc. to induce different chemical reactions so as to vary the transients;

Use of curve fitting methods to extract or sample information from the obtained set of transients;

Use of various multivariate signal-processing methods to interpret the information gained thereby.

Particularly, said method teaches that only or mainly the first part of the response transient is measured and used. Thereby, a very rapid testing or tasting can be carried out since the first part of the transient is of a very short duration. With the first part is here meant the initial rising slope up to the peak.

In EP application number: 00128297.9 (hereafter referred to as EP '297) the applicants disclose an ozone sensor based on the ideas of WO 99/13325. It is shown in EP '297 that satisfying results concerning detection of ozone may be achieved by performing pulsed voltammetric measurements using a single working electrode of Rh. But it is further shown that the overall performance of a four-electrode sensor is better than a sensor with a single electrode of Rh. Therefore, the preferred embodiment of this novel ozone sensor is a sensor device with a multiple working-electrode arrangement, wherein each working electrode is made of a different material than the others. The EP '297 publication is incorporated herein in its entirety by reference.

However, the pulse-sequences for voltammetric measurements shown both in WO 99/13325 and EP '297 involve many pulse-steps and are therefore time consuming, especially if multi-electrode arrangements are used, whereby each pulse-sequence have to be repeated for each electrode.

SUMMARY OF THE INVENTION

The object of the invention is to provide a new method for voltammetric characterization of a liquid sample and a system for voltammetric characterization, which method and system overcomes one or more drawbacks of the prior art.

This is achieved by the method for voltammetric characterization of a liquid sample, using a voltammetric setup comprising at least two working electrodes and a counter electrode that are placed in contact with the liquid sample, the method comprising the steps of: a. applying a first potential on all working-electrodes, b. performing a number of voltammetric cycles according to a predetermined pulse-sequence, each comprising the steps of: i. applying a second potential on the counter electrode according to the pulse-sequence, ii. performing a predetermined number of measurement procedures, each comprising the steps of: removing said applied first potential from all but one of the working electrodes, registering the current passing through the working electrode still having said first potential applied thereto, storing the registered value in a data storage unit, applying the first potential on all working electrodes, and c. analyzing said stored values using a predetermined mathematical model to produce a result.

There is also provided a system for voltammetric characterization, comprising: at least two working electrodes, a working electrode selecting unit enabling connection and disconnection of one or more of the working electrodes to a first potential, a counter electrode connected to a second potential, a current registration unit, arranged to register the current passed through the working electrode(s) connected to said first potential, a control unit arranged to control said second potential, said working electrode selecting unit and to read current values from said current registration unit at predetermined points in time, a data storage unit for storing said current values, and a processing unit arranged to analyze the stored current values using a predetermined mathematical model, and to output the result from the analysis.

One advantage with such a method and system is that the time needed for the voltammetric detections is reduced to a great extent.

Another advantage is that the system may be produced as an integrated device, thus providing a fully functional, compact system at a low cost.

Embodiments of the invention are defined in the dependent claims.

BRIEF DESCRIPTION OF THE DRAWINGS

The invention will be described in detail below with reference to the drawings, in which FIG. 1 schematically shows a system according to the present invention.

DETAILED DESCRIPTION OF PREFERRED EMBODIMENTS

The present invention is aimed at facilitating voltammetric characterization according to WO 99/13325 and/or EP '297 utilizing multiple working-electrodes, i.e. two or more working electrodes. As mentioned above, the number of working-electrodes in such systems may be very large, but in order to keep the amount of registered data at a reasonable level a preferred embodiment of the sensor device comprises four working-electrodes.

Figure 1:
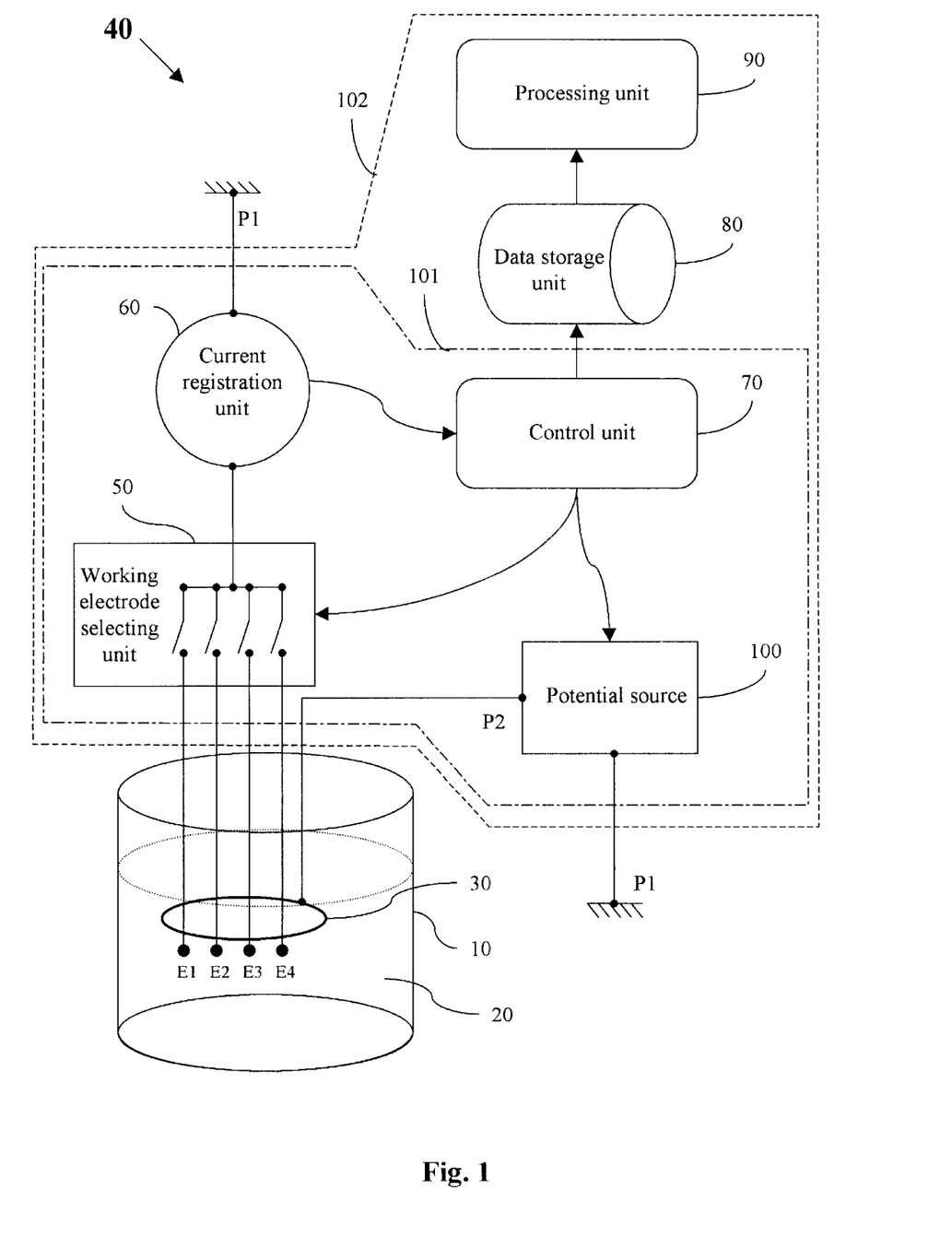

The invention will now be described with reference to an embodiment of a voltammetric system comprising four working-electrodes as is shown in FIG. 1. The setup includes a sample reservoir 10 containing a sample 20 that is to be analyzed. This reservoir 10 can be of a stationary type or designed as a flow cell. Four working electrodes E1, E2, E3 and E4 are immersed in the sample liquid 20. The working-electrodes E1–E4 can be made of any metal or alloy that yields the desired effect; preferably each of the electrodes is made of a different material.

In a preferred embodiment, the measurement set up further comprises a counter electrode 30 (auxiliary electrode) (i.e. a standard two-electrode voltammetric setup). Alternatively a standard three-electrode system can be employed, i.e. working electrodes E1–E4, a counter electrode 30 and a reference electrode. If the apparatus or system, in which the invention is implemented, is itself made of e.g. stainless steel, the apparatus housing could be used as counter electrode 30. Other materials for the counter electrode 30 are of course conceivable, e.g. Pt, Au. The working electrodes E1–E4 are preferably integrated in a sensor device and possibly also the counter electrode 30.

Figure 2:
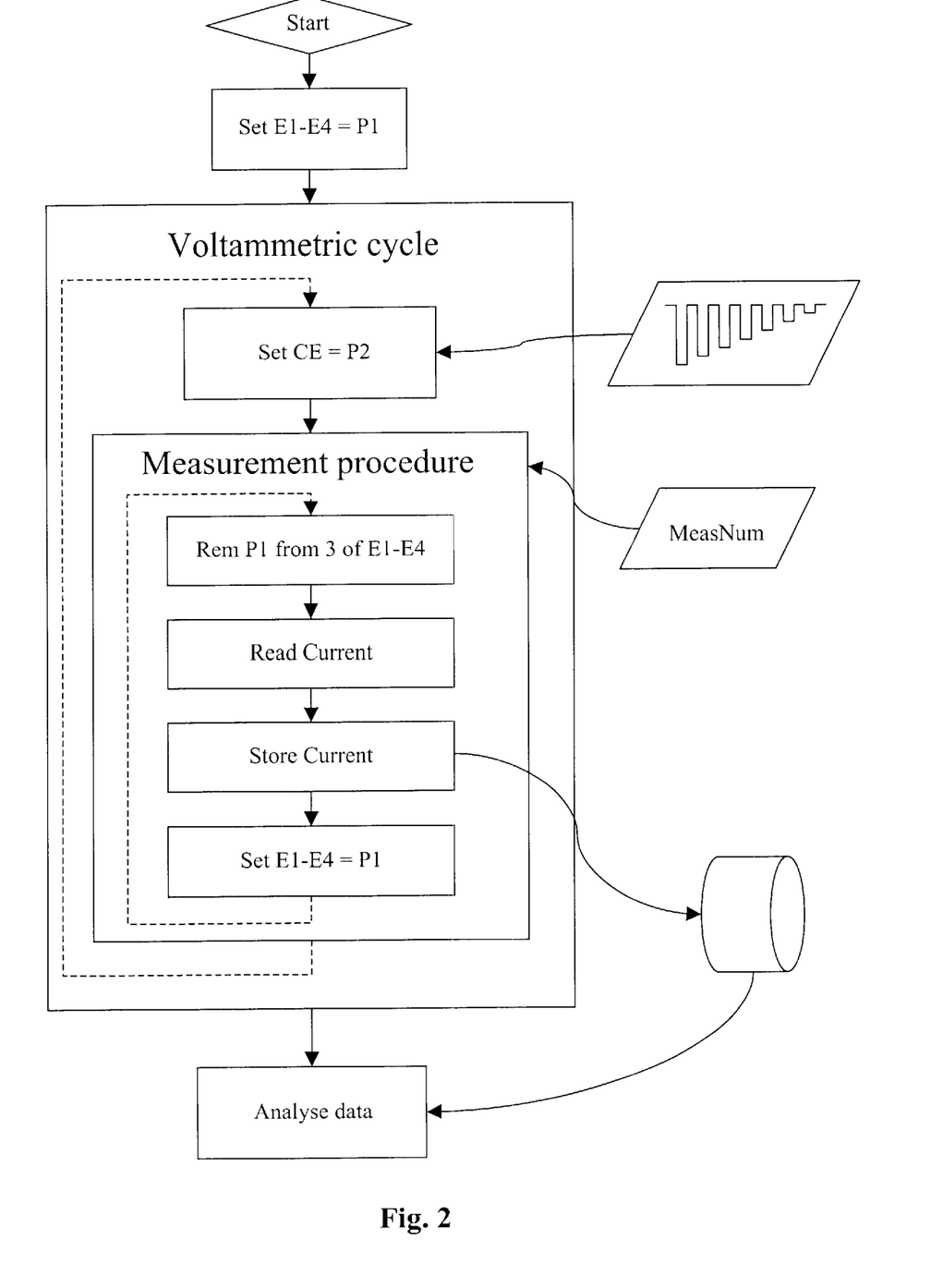
FIG. 2 is a schematic diagram of a preferred embodiment of the method according to the present invention.

The method for voltammetric characterization according to the present invention enables parallel measurements on a plurality of working electrodes E1–E4 during the same pulse-sequence. A schematic diagram of a preferred embodiment of the method is shown in FIG. 2 and it comprises the following steps:

a applying a first potential P1 on all working-electrodes E1–E4, b performing a number of voltammetric cycles according to a predetermined pulse-sequence, each comprising the steps of:
   i applying a second potential P2 on the counter electrode 30 according to the pulse-sequence,
   ii performing a predetermined number of measurement procedures, each comprising the steps of:
      removing said applied first potential P1 from all but one of the working electrodes E1–E4,
      registering the current passing through the working electrode E1, E2, E3 or E4 still having said first potential P1 applied thereto,
      storing the registered value in a data storage unit,
      applying the first potential P1 on all working electrodes, and c analyzing said stored values using a predetermined mathematical model to produce a result.

Figure 3:
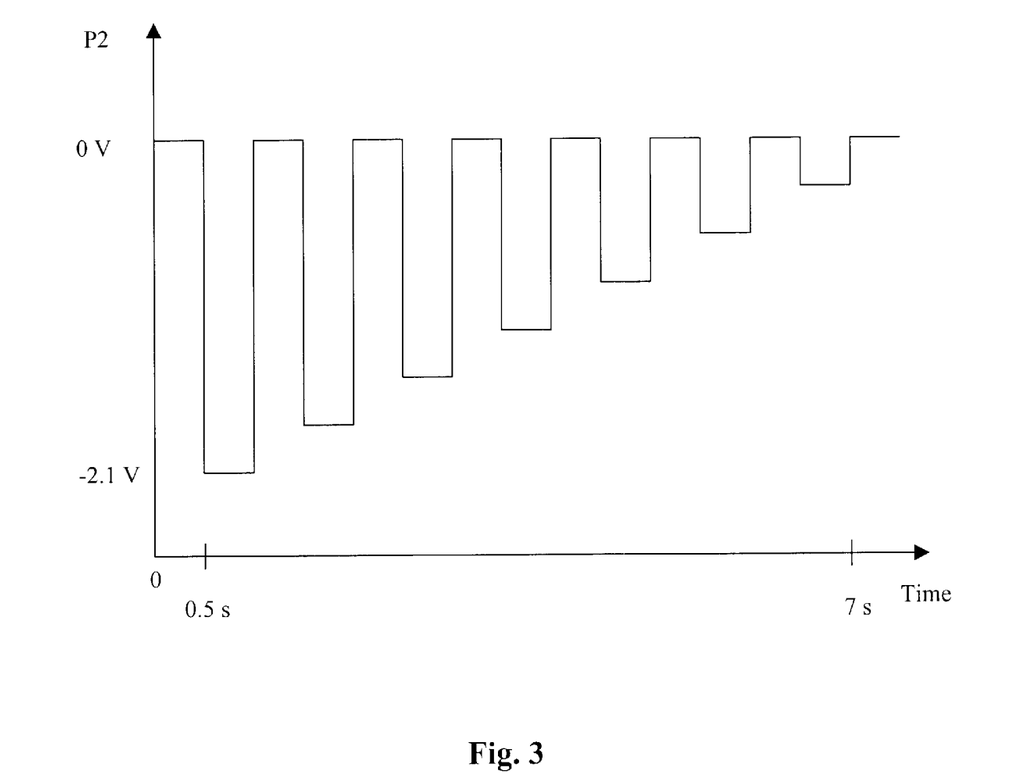
FIG. 3 shows a pulse sequence usable with the invention.

As is described both in WO 99/13325 and EP '297 the predefined pulse-sequence used may comprise any suitable pulse-sequence. FIG. 3 shows an exemplary pulse-sequence, which may be referred to as Large Amplitude Pulse Voltammetry (LAPV)

Figure 4:
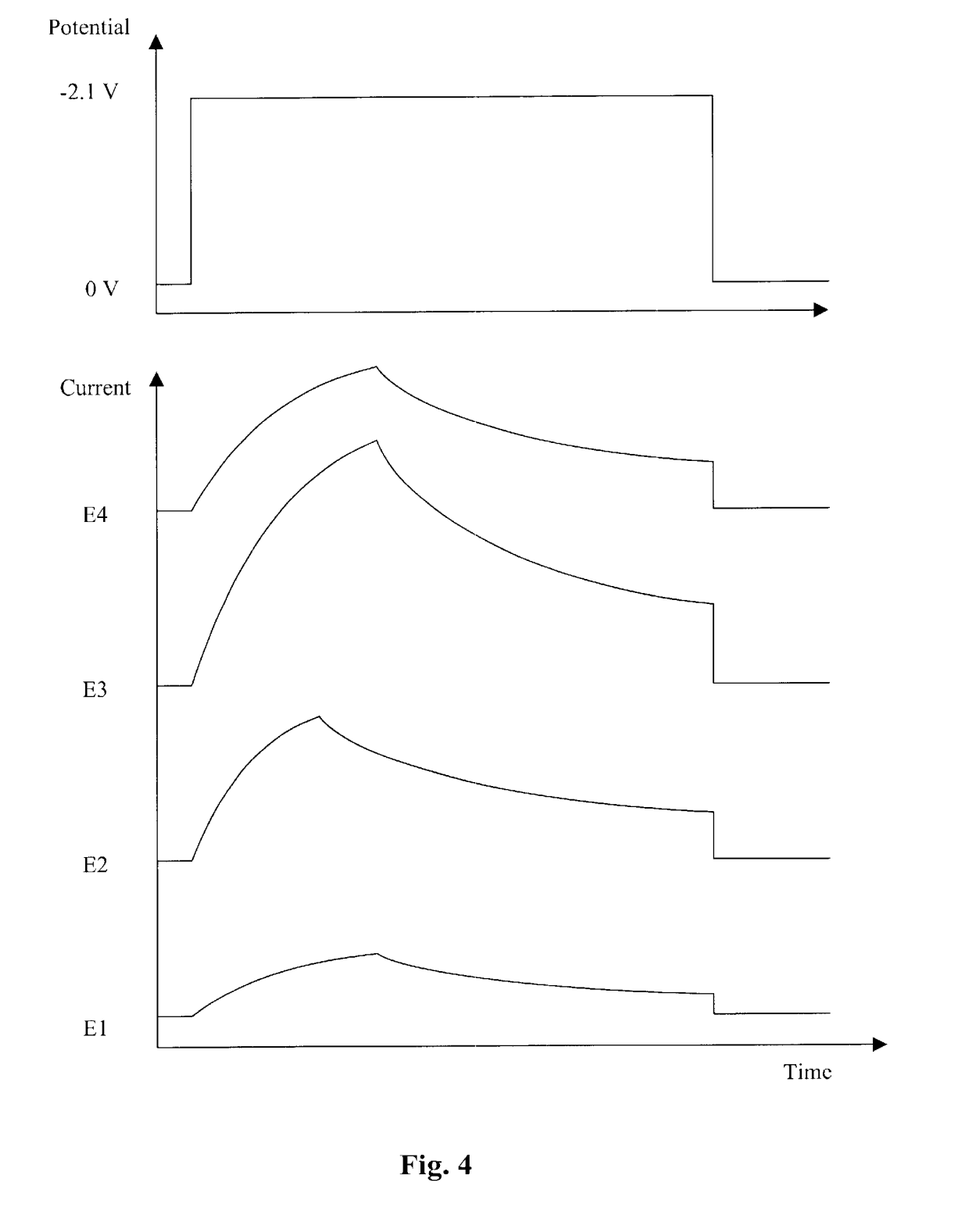
FIG. 4 shows an exemplary voltammetric cycle for four working electrodes.

The LAPV pulse-sequence shown in FIG. 3 has a pulse-duration of 0.5 s and the first pulse has a potential of −2.1 V. The potential of the subsequent pulses is thereafter raised 300 mV for each pulse until 0 V is reached. After each pulse the potential is set to 0 V for 0.5 s before the next pulse starts. Throughout this application the voltammetric measurements that are performed during one pulse in the pulse-sequence is referred to as a voltammetric cycle. FIG. 4 shows an exemplary voltammetric cycle, wherein E1–E4 refers to the four working electrodes respectively. Further, the potentials prescribed in the pulse-sequence refer to the difference between the first and the second potential (P1–P2) in the above method. Preferably, the first potential P1 is set to 0 V (ground) and the second potential P2 is varied according to the pulse-sequence. However, it may also be the other way around, which is obvious for anyone familiar with the field of voltammetry.

Figure 5:
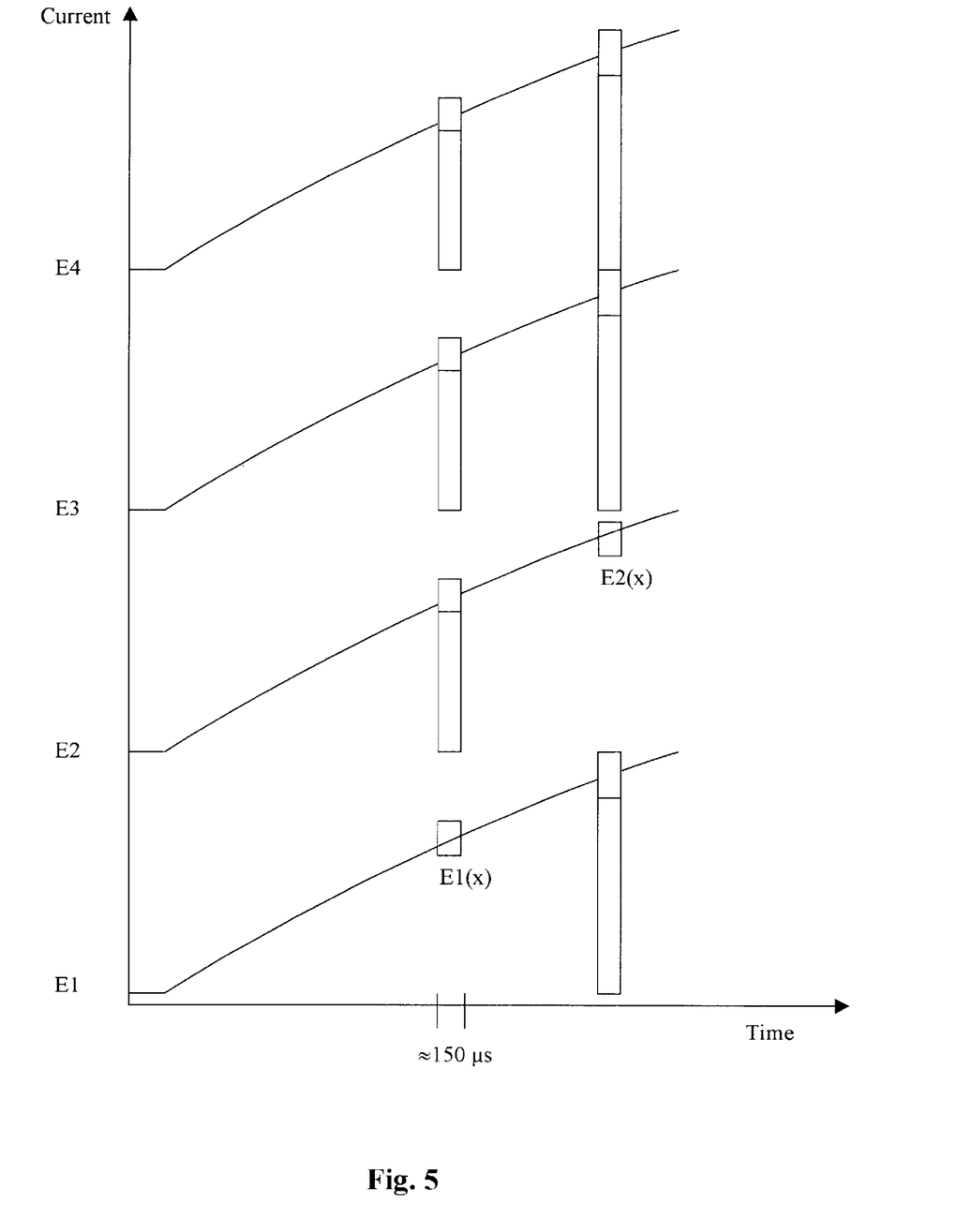
FIG. 5 illustrates two measurement procedures according to the method of the present invention.

The main requirement on the method according to the invention is that each measurement procedure is fast enough, such that the voltammetric cycles for the "disconnected" working electrodes are essentially unaffected. FIG. 5 illustrates two measurement procedures during a part of a voltammetric cycle. It has been shown that measurement procedures with duration in the range of 150 $\mu$s fulfill this requirement.

Alternatively one could envisage a method wherein the measurement procedure is performed in a parallel mode for all four working electrodes E1–E4 where all electrodes are connected to the first potential P1 throughout the whole voltammetric cycle. However, such a method may encounter problems associated with interaction between the working electrodes E1–E4, as all working electrodes E1–E4 are participating in the electrochemical process during the measurement. Furthermore, in such a system each working electrode E1–E4 requires a separate current registration unit, which may lead to calibration errors due to small differences in the characteristics of the separate current registration units, compared to the setup according to the present invention where one single current registration unit us used for all four working electrodes (see below for detailed description).

The number of measurement procedures and timing of the same during the voltammetric cycle is adapted to the specific case, and is not critical to the method. The number of measurement procedures needed to achieve a desired accuracy can be very different from case to case. In certain cases perhaps it is sufficient with four points, in other circumstances of the order of 100 points could be relevant. If, for example, 19 measurement procedures are performed for each working electrode E1–E4 in a 4 working electrode arrangement, the total number of recorded current values for each voltammetric cycle is 76, and if the pulse-sequence comprises 7 pulses, this results in 532 current values. In one embodiment the measurement procedures may be performed in a straightforward repetitive sequence for the four working electrodes E1 to E4. Alternatively the measurement procedures for each working electrode E1–E4 are performed independently of the measurement procedures for the other working electrodes E1–E4, such that optimum results are acquired for each electrode.

In the last step of the method the recorded current values are analyzed according to the teaching of WO 99/13325 and EP '297. Alternatively a large number of experimental data sets are used to produce a mathematical model that eliminates the time consuming step of multivariate analysis to achieve a result. The mathematical model may for instance have the form:

$$Y = B0 + B1 \cdot X1 + B2 \cdot X2 + B3 \cdot X3$$

where Y is a number that for instance indicates the concentration of the species to be detected, e.g. ozone, urea . . . , X1 . . . are the recorded current values for the measurement procedure of the same number, B0, B1 . . . are fitted constants for each recorded current value of same number. To further reduce the complexity of the mathematical model the least significant terms in the above expression may be omitted.

In order to optimize the result obtained from the method it may be necessary to record a number of other parameters for the medium to be characterized. Such parameters may be temperature and conductivity. The temperature of the medium is preferably recorded by adding a temperature sensor to the sensor device. The conductivity is preferably recorded using the existing electrode arrangement before the voltammetric characterization is initiated. The conductivity may for instance be determined using a pulse-sequence consisting of 10 pulses with alternating potentials of ±200 mV and duration of 50 ms.

In order to perform said method for voltammetric characterization, a system for voltammetric characterization 40 has been developed. One preferred embodiment of this system 40 comprises a working electrode selecting unit 50, a current registration unit 60, a control unit 70, a data storage unit 80 and a processing unit 90 (FIG. 1).

The working electrode selecting unit 50 is connected to the four working electrodes E1–E4 and to the first potential P1, and it is arranged to connect one or more of the working electrodes E1–E4 to the first potential P1. In a normal mode all four working electrodes E1–E4 are connected to the first potential P1, but during the current registration step of the measurement procedure three of the working electrodes E1–E4 are disconnected. As mentioned above, one primary requirement on the working electrode selecting unit 50 is that the connection/disconnection of working electrodes E1–E4 is extremely fast. In one preferred embodiment, the working electrode selecting unit 50 is comprised of a commercially available four channel analog switch, such as max 312 from The current registration unit 60 is arranged to register the current flowing between said first potential P1 to the working electrode selecting unit 50. The registered current is the same that is passed through the connected working electrode (s) E1–E4, and as only one electrode is connected during the current registration step of each measurement procedure, the value registered by the current registration unit is the current value used for the voltammetric characterization. In one preferred embodiment, the current registration unit 60 is comprised of a current amplifier, producing an output representative of the current.

The control unit 70 is arranged to control said second potential P2, said working electrode selecting unit and to read current values from said current registration unit 60 at predetermined points in time. Hence, a control cycle (according to the method of the invention) for the control unit comprises, setting the second potential P2, controlling the working electrode selecting unit 50 to connect/disconnect working electrodes E1–E4, and reading current values from the current registration unit 60. To achieve this, the control unit 70 either comprises a memory unit wherein control software is stored, or a control-interface such that it in turn is controlled by an external process control system. In one preferred embodiment, the control unit 70 is comprised of a commercially available micro controller unit (MCU) such as PIC 16C877 from Microchip.

The second potential P2 is preferably supplied by a controllable variable potential source 100. One preferred embodiment of a suitable potential source 100 is an 8-bit digital to analogue converter combined with an amplifier capable of setting the polarity of the potential, and finally a buffer capable of producing a stable output.

The data storage unit 80 is used for storing the recorded current values, and in one preferred embodiment, it is comprised of a commercially available memory circuit such as D43256 from NEC.

The processing unit 90 is arranged to analyze the stored current values using a predetermined mathematical model, such as the one specified above. The result from the analysis is thereafter output as a digital or analogue value, via a display or the like. In one preferred embodiment, the processing unit 90 is comprised of a commercially available micro controller unit (MCU) such as PIC 16C877 from Microchip.

In another embodiment of the invention, the working electrode selecting unit 50, the current registration unit 60, and the control unit 70 are integrated as one measuring device 101 that is arranged to output the read current values to an external data storage 80 and processing unit 90. This embodiment may further include that the control unit 70 is externally controlled by said external data storage 80 and processing unit 90, whereby an inexpensive and extremely versatile system for voltammetric characterization 40 is achieved. Such a system 40 may further be used to find appropriate pulse-sequence and voltammetric settings when preparing the system 40 for use with new working electrode arrangements, sample types, species to detect, or the like. The ways by which such adaptations are performed are clear from WO 99/13325 and EP '297.

Systems for voltammetric characterization 40 that are designated for characterizing of specified species in a specific medium are preferably fully integrated, i.e. the working electrode selecting unit 50, the current registration unit 60, the control unit 70, the data storage unit 80 and the processing unit 90 are all integrated as one characterization device 102 arranged to output the result from the analysis. Such systems 40 are especially suitable as "embedded" sensors in larger systems where it is of importance to continuously analyze the process or the like, e.g. ozone sensor in a system for sterilization of materials, (e.g. preparations for medical use) where ozone is used for eliminating harmful and unwanted species. The output from such an embedded sensor is then used as input in the system control for controlling the process.

The skilled man could envisage several other variations and modifications of the actual arrangement and configuration of the method and the system according to the present invention, all of which are intended to fall within the scope of the attached claims.

A great advantage of the method and system according to the present invention is that it is suitable for on-line measurements, such as monitoring of quality in a food manufacturing process, concentration of a specific species in a chemical process.

What is claimed is:

1. A method for voltammetric characterization of a liquid sample using a voltammetric setup comprising at least two working electrodes and a counter electrode placed in contact with the liquid sample, the method comprising the steps of:
   a. applying a first potential on the at least two working electrodes;
   b. performing at least one voltammetric cycle according to a predetermined pulse-sequence, each of the at least one voltammetric cycle comprising the steps of:
      i. applying a second potential on the counter electrode according to the pulse-sequence; and
      ii. performing at least one measurement procedure, each of the at least one measurement procedure comprising the steps of:
         removing said first potential from all but one of the at least two working electrodes;
         registering the current passing through the working electrode still having said first potential applied thereto to obtain a registered value;
         storing the registered value in a data storage unit; and
         applying the first potential on the at least two working electrodes; and c. analyzing said stored values using a predetermined mathematical model to produce a result.

2. The method for voltammetric characterization according to claim 1, wherein the first potential (P1) is zero volt.

3. The method for voltammetric characterization according to claim 1, wherein the predetermined mathematical model is produced using multivariate analysis on a plurality of experimental data sets.

4. The method for voltammetric characterization according to claim 1, wherein the result is the concentration of one specific species in the sample.

5. The method for voltammetric characterization according to claim 1, wherein the result is the concentration of ozone in the sample.

6. The method for voltammetric characterization according to claim 1, wherein the result is the concentration of urea in the sample.

7. A system for voltammetric characterization comprising:
   at least two working electrodes;
   a working electrode selecting unit adapted to connect the at least two working electrodes to a first potential at the same time and adapted to disconnect all but one of the at least two working electrodes from the first potential for a measurement procedure;
   a counter electrode connected to a second potential;
   a current registration unit arranged to register current passed through the working electrode connected to said first potential;
   a control unit arranged to control said second potential and said working electrode selecting unit, said control unit further arranged to read current values from said current registration unit at predetermined points in time,
   a data storage unit for storing said current values; and
   a processing unit arranged to analyze the stored current values using a predetermined mathematical model and to output a result from the analysis.

8. The system for voltammetric characterization according to claim 7, wherein the working electrode selecting unit, the current registration unit, and the control unit are integrated as one measuring device arranged to output the read current values to an external data storage unit and processing unit.

9. The system for voltammetric characterization according to claim 7, wherein the working electrode selecting unit, the current registration unit, the control unit, the data storage unit and the processing unit are integrated as one characterization device arranged to output the result from the analysis.

10. The system for voltammetric characterization according to claim 7, wherein the working electrode selecting unit has a switch time that permits measurement procedures with a duration in the order of 150 $\mu$s to be performed.

* * * * *

UNITED STATES PATENT AND TRADEMARK OFFICE
CERTIFICATE OF CORRECTION

PATENT NO.     : 6,664,776 B2
DATED          : December 16, 2003
INVENTOR(S)    : Arnold Olofsson It is certified that error appears in the above-identified patent and that said Letters Patent is hereby corrected as shown below:

<u>Drawings,</u>
Please delete Figure 5 and replace with the attached Figure 5.

Signed and Sealed this

Twenty-fourth Day of August, 2004

JON W. DUDAS
*Director of the United States Patent and Trademark Office*

Fig. 5